United States Patent
Loganathan (10) Patent No.: US 10,617,436 B2
(45) Date of Patent: Apr. 14, 2020

(54) EMBOLECTOMY DEVICES AND METHODS

(71) Applicants: STRYKER CORPORATION, Kalamazoo, MI (US); STRYKER EUROPEAN HOLDINGS I, LLC, Kalamazoo, MI (US)

(72) Inventor: Siddharth Loganathan, Santa Clara, CA (US)

(73) Assignee: Stryker, Inc., Kalamazoo, MI (US)

( * ) Notice: Subject to any disclaimer, the term of this patent is extended or adjusted under 35 U.S.C. 154(b) by 210 days.

(21) Appl. No.: 15/808,532

(22) Filed: Nov. 9, 2017

(65) Prior Publication Data
US 2018/0064456 A1 Mar. 8, 2018

Related U.S. Application Data

(63) Continuation of application No. 15/097,625, filed on Apr. 13, 2016, now Pat. No. 10,314,602.

(Continued)

(51) Int. Cl.
*A61B 17/221* (2006.01)
*A61B 17/3207* (2006.01)
*A61B 17/00* (2006.01)

(52) U.S. Cl.
CPC .... *A61B 17/221* (2013.01); *A61B 17/320725* (2013.01); *A61B 2017/00004* (2013.01); *A61B 2017/00411* (2013.01); *A61B 2017/00778* (2013.01); *A61B 2017/00867* (2013.01); *A61B 2017/00898* (2013.01)

(58) Field of Classification Search
CPC .......... A61B 17/221; A61B 17/320725; A61B 2017/00867; A61B 2017/00004; A61B 2017/0411; A61B 2017/00778; A61B 2017/00898
See application file for complete search history.

(56) References Cited

U.S. PATENT DOCUMENTS 5,780,807 A 7/1998 Saunders
5,904,698 A 5/1999 Thomas et al.
(Continued)

FOREIGN PATENT DOCUMENTS

EP 2959853 12/2015
WO 2012/085073 A2 6/2012
WO 2014/127738 8/2014

OTHER PUBLICATIONS

Foreign Office Action with Search Report for Chinese Appln. No. 201680021922.8, dated Aug. 1, 2019, including English translation provided by Chinese associate, (14 pages).

(Continued)

*Primary Examiner* — George J Ulsh
(74) *Attorney, Agent, or Firm* — Vista IP Law Group, LLP (57) ABSTRACT

An embolectomy device includes a tubular body having a plurality of interconnected primary struts that define a plurality of openings when the tubular body is in a radially expanded deployed configuration, and a plurality of secondary struts connected to the primary struts that move from being aligned with the primary struts to a non-aligned configuration in which the secondary struts extend at least partially into and/or across the openings, to thereby ensnare or encapsulate a vascular obstruction within the primary and secondary struts after the tubular body is deployed proximate the obstruction and allowed to expand into or through the obstruction.

3 Claims, 8 Drawing Sheets

Related U.S. Application Data

(60) Provisional application No. 62/148,359, filed on Apr. 16, 2015.

(56) References Cited

U.S. PATENT DOCUMENTS

| | | |
|---|---|---|
| 5,906,759 A | 5/1999 | Richter |
| 5,922,005 A | 7/1999 | Richter et al. |
| 6,563,080 B2 | 5/2003 | Shapovalov |
| 8,444,661 B2 | 5/2013 | Nair et al. |
| 8,460,313 B2 | 6/2013 | Huffmaster |
| 8,486,104 B2 | 7/2013 | Samson et al. |
| 8,795,317 B2 | 8/2014 | Grandfield et al. |
| 2002/0010487 A1 | 1/2002 | Evans et al. |
| 2011/0184456 A1 | 7/2011 | Grandfield et al. |
| 2012/0083868 A1 | 4/2012 | Shrivastava et al. |

OTHER PUBLICATIONS

English Translation of claims for Search Report for Chinese Appln. No. 201680021922.8, dated Aug. 1, 2019.
PCT International Search Report and Written Opinion for International Application No. PCT/US2016/027249, Applicant Stryker Corporation, forms PCT/ISA/210, 220, and 237, dated Jun. 16, 2016 (11 pages).
Examination Report dated Feb. 2, 2019 for EP Appln. No. 16717810.2-113.
Response and Amendment to Examination Report filed Mar. 13, 2019 for EP Appln. 16717810.2-1113.

EMBOLECTOMY DEVICES AND METHODS

RELATED APPLICATION DATA

The present application is a continuation of U.S. patent application Ser. No. 15/097,625, filed Apr. 13, 2016, which claims the benefit under 35 U.S.C. § 119 to U.S. provisional patent application Ser. No. 62/148,359, filed Apr. 16, 2015. The foregoing applications are hereby incorporated by reference into the present application in their entirety.

FIELD

The disclosed inventions relate generally to medical devices for treating embolic stroke. In particular, the disclosed inventions relate to medical devices for removing embolic obstructions from the vasculature of a patient, and methods for removing vascular obstructions using same.

BACKGROUND

It is not uncommon for thrombi to form in a vessel. Sometimes, such clots are harmlessly dissolved in the blood stream. At other times, however, such clots may lodge in a blood vessel, where they can partially or completely occlude the flow of blood. If the partially or completely occluded vessel feeds blood to sensitive tissue such as, the brain, lungs or heart, for example, serious tissue damage may result. Such ischemic events may also be exacerbated by atherosclerosis, a vascular disease that causes the vessels to become narrowed and tortuous. The narrowing or increased tortuousness of the vessel may, in certain circumstances, lead to the formation of atherosclerotic plaque, which can cause further complications in the body. Embolectomy devices such as inflatable catheters and clot pullers are used in a variety of applications to remove blood clots or other foreign bodies from a blood vessel such as an artery or vein.

In an embolectomy procedure for removing a blood clot from a patient's blood vessel, a delivery catheter or sheath is typically inserted percutaneously into the patient's vasculature, e.g. via the femoral, jugular or antecubital veins, by so-called minimally invasive techniques, and advanced to a target site within the vessel containing the clot. To ascertain the precise location of the blood clot within the vessel, radiopaque dye may be injected into the vessel permitting the occluded blood vessel to be radiographically visualized with the aid of a fluoroscope. For example, a Fogarty catheter or other suitable delivery device may be used to transport the embolectomy device in a collapsed position distal the site of the clot. Many delivery devices include sheaths or catheters, and delivery members fixed to the embolectomy device to push and pull embolectomy device through the sheaths and catheters. Catheter and delivery members may be configured to be bent without breaking while navigating through tortuous vasculature. The catheter is delivered to the site where it is required through the patient's skin or by a "cut down" technique in which the blood vessel concerned is exposed by minor surgical means.

An embolectomy device is compressed radially inwards and delivered through the catheter for positioning adjacent to the clot to be removed. The embolectomy device is then pushed distally relative to the catheter, or the catheter is withdrawn proximally relative to the embolectomy device (or some of each), in order to deploy the embolectomy device out of the catheter and into the blood vessel, allowing the no-longer radially constrained embolectomy device to radially expand to a predetermined diameter within the blood vessel. The expanded embolectomy device is then urged in a proximal direction to ensnare and remove the clot from the vessel wall. A wire basket, coil, membrane or other collector element can be used to capture the clot as it is dislodged from the vessel wall. Clot capture strategies include increased axial friction from radially expansile force, snaring/encapsulation/entrapment, integration, and envelopment. The characteristics of the clot, the vascular location and the removal device determine the strategy or combination of strategies used in each clot removal. Once captured by the collector element, the embolectomy device and captured blood clot are then loaded into a retrieval device and withdrawn from the patient's body. In certain applications, the removal of the foreign object within the vessel may cause emboli to migrate downstream and enter other branching passageways within the body. To prevent migration of emboli downstream, it may be necessary to temporarily impede or obstruct the flow of blood distal to the therapeutic site while retrieving the embolectomy device.

Embolectomy devices are generally tubular devices for insertion into body lumens. However, it should be noted that embolectomy may be provided in a wide variety of sizes and shapes. Self-expanding embolectomy device expand when unconstrained, without requiring any further input. A self-expanding embolectomy device may be biased so as to expand upon release from the delivery catheter and/or include a shape-memory component which allows the stent to expand upon exposure to a predetermined condition. Self-expanding embolectomy device are biased to an expanded configuration. Embolectomy devices can be made from a variety of materials, including metals and polymers. Embolectomy devices can be made from shape memory materials, such as shape memory metals (e.g., Nitinol) and polymers (e.g., polyurethane). Such shape memory embolectomy devices can be induced (e.g., by temperature, electrical or magnetic field or light) to take on a shape (e.g., a radially expanded shape) after delivery to a treatment site. Other embolectomy device materials include stainless steel, and Elgiloy.

Embolectomy devices are typically cylindrical scaffolds formed from a set of elongate elements (i.e., struts). The struts can interconnect in a repeating pattern or in a random manner. The scaffolding can be woven from wires, cut out of tubes, or cut out of sheets of material that are subsequently rolled into a tube. Tubes and sheets from which stents are cut as also known as stent "preforms." The manner in which an embolectomy device's struts interconnect determines its longitudinal and radial rigidity and flexibility. Radial rigidity is needed to provide the radial force needed to engage the clot, but radial flexibility is needed to facilitate radial compression of a stent for delivery. Longitudinal rigidity is needed to pull an engaged clot from the vessel, but longitudinal flexibility is needed to facilitate delivery of the stent (e.g., through tortuous vasculature). Embolectomy device patterns are typically designed to maintain an optimal balance between longitudinal and radial rigidity and flexibility for the embolectomy device.

Embolectomy devices can be cut from tubes and sheets using a variety of techniques, including laser cutting or etching a pattern onto a tube or sheet to form struts from the remaining material. Lasers cutting or etching may be performed on a sheet, which is then rolled into a tube, or a desired pattern may be directly cut or etched into a tube. Other techniques involve forming a desired pattern into a sheet or a tube by chemical etching or electrical discharge machining. Laser cutting of stents, which are structurally similar to embolectomy devices, has been described in a number of publications including U.S. Pat. No. 5,780,807 to Saunders, U.S. Pat. Nos. 5,922,005 and 5,906,759 to Richter and U.S. Pat. No. 6,563,080 to Shapovalov, the entire disclosures of which are incorporated herein by reference, as though set forth in full. Embolectomy devices may also include components that are welded, bonded or otherwise engaged to one another.

SUMMARY

In accordance with the disclosed embodiments, an exemplary embolectomy device includes a tubular body having a radially collapsed delivery configuration and a radially expanded deployed configuration, the tubular body comprising a plurality of interconnected primary struts that define a plurality of openings when the tubular body is in the radially expanded deployed configuration. A plurality of secondary struts are connected to the primary struts, wherein the secondary struts move from an aligned configuration in which the secondary struts are aligned or substantially aligned with respective primary struts to a non-aligned configuration in which the secondary struts extend away from the primary struts and at least partially into and/or across the openings of the expanded tubular body. In this manner, when the tubular body is delivered to a targeted vascular site proximate an obstruction, and moved or allowed to move from the radially collapsed delivery configuration to the radially expanded deployed configuration by expanding radially into or through the vascular obstruction, the secondary struts move, be moved, or be allowed to move, respectively, from the aligned configuration to the non-aligned configuration to thereby ensnare or encapsulate the vascular obstruction or portions thereof between or within the primary and secondary struts.

In some embodiments, the secondary struts are constrained on the primary struts when the tubular body is in the radially collapsed delivery configuration, and are released to self-move from the aligned configuration to the nonaligned configuration when the tubular body is in the radially expanded deployed configuration, or as the tubular body moves from the radially collapsed delivery configuration to the radially expanded deployed configuration. By way of non-limiting examples, the secondary struts may be constrained by mechanical structures on the primary struts, by an adhesive bond that dissolves when the tubular body is deployed, or by respective links that may be electrolytically dissolved when the tubular body is deployed at the vascular site.

In other embodiments, the secondary struts self-move from the aligned configuration to the non-aligned configuration due to a change in temperature when the tubular body is deployed at the vascular site, or upon application of an electrical current when the tubular body is deployed at the vascular site. In still other embodiments, the secondary struts self-move from the aligned configuration to the non-aligned configuration more slowly than the primary struts self-move from the radially collapsed delivery configuration to the radially expanded deployed configuration, due to respective physical characteristics of the primary and secondary struts. For example, the secondary struts may be thicker than the primary struts.

In accordance with further disclosed embodiments, an exemplary embolectomy device for removing an obstruction from a vascular site includes a tubular body having a radially collapsed delivery configuration and a radially expanded deployed configuration, the tubular body comprising a plurality of interconnected struts that define a plurality of openings when the tubular body is in the radially expanded deployed configuration. The struts comprise a substance that enables thickening of the struts to thereby reduce a size of the respective openings after the tubular body is deployed at the vascular site, such that, when the tubular body is delivered to a targeted vascular site proximate an obstruction, and moved or allowed to move from the radially collapsed delivery configuration to the radially expanded deployed configuration by expanding radially into or through the vascular obstruction, the struts thicken, or may be thickened, to thereby ensnare or encapsulate the vascular obstruction or portions thereof between or within the thickened struts.

In one such embodiment, the struts are coated with a material that causes blood to coagulate thereon to thereby thicken the struts after the tubular body is deployed at the vascular site. In another embodiment, the struts are made of a metal or metal alloy that oxidizes to thereby thicken the struts after the tubular body is deployed at the vascular site. In yet another embodiment, the struts are made of a metal or metal alloy that thickens the struts via ionic attraction due to an electrical current applied to the tubular body after the tubular body is deployed at the vascular site.

In accordance with a further disclosed embodiment, an exemplary embolectomy device for removing an obstruction from a vascular site includes a first tubular body having a radially collapsed configuration and a radially expanded configuration, and a second tubular body having a radially collapsed configuration and a radially expanded configuration, the first and second tubular bodies disposed in a coaxial formation and mechanically coupled with an actuator that moves one of the first and second tubular bodies axially relative to the other one. The first tubular body comprises a first plurality of interconnected struts that define a first plurality of openings when the first tubular body is in the radially expanded configuration, and the second tubular body comprises a second plurality of interconnected struts that define a second plurality of openings when the second tubular body is in the radially expanded configuration. The embolectomy device has a delivery configuration in which the first and second tubular bodies are in their respective radially collapsed configurations; a deployed configuration in which the first and second tubular bodies are in their respective radially expanded configurations with the first pluralities of struts and openings aligned or substantially aligned with the respective second pluralities of struts and openings; and an actuated configuration in which one of the first and second tubular bodies is moved axially relative to the other one by the actuator so that first pluralities of struts and openings are off-set with the respective second pluralities of struts and openings. In this manner, when the embolectomy device is (i) delivered to a targeted vascular site proximate an obstruction, (ii) moved or allowed to move from the delivery configuration to the deployed configuration with the respective first and second tubular bodies expanding radially into or through the vascular obstruction, and (iii) thereafter moved from the deployed configuration to the actuated configuration, portions of the vascular obstruction become ensnared and/or encapsulated between or within the respective first and second pluralities of struts.

Various methods using the above-described and other disclosed embodiments for removal of a vascular obstruction, as well as other and further aspects and features of the disclosed embodiments will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

DETAILED DESCRIPTION OF THE ILLUSTRATED EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skilled in the art would consider equivalent to the recited value (i.e., having the same function or result). In many instances, the terms "about" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Current embolectomy devices typically expand radially outward after delivery to ensnare adjacent vascular obstructions (e.g., emboli). However, vascular obstructions can detach from current embolectomy devices during withdrawal of the embolectomy devices to remove the ensnared vascular obstructions, resulting in a failed embolectomy procedure. Failed embolectomy procedures that disturb vascular obstructions can exacerbate embolic episode by moving emboli into more distal (and smaller) vessels and by generating additional emboli through fragmentation.

In embolectomy devices constructed according to the disclosed embodiments, after radial expansion, the pore of the embolectomy devices are reduced in size by one or more strut-related changes including, but not limited to: (1) changes in the strut configuration; (2) changes in strut size; and (3) relative strut movement. In some embodiments, reduction of embolectomy device pore size improves ensnarement of vascular obstructions by embolectomy devices, thereby reducing the probability of detachment during withdrawal. In other embodiments, reduction of embolectomy device pore size improves envelopment of vascular obstructions by embolectomy devices, thereby reducing the probability than enveloped portions of vascular obstructions will escape the embolectomy device during withdrawal of the embolectomy devices to remove the enveloped vascular obstructions. In each of the disclosed embodiments, a strut-related change reduces embolectomy device pore size to facilitate removal of vascular obstruction using the embolectomy device by improving ensnarement or envelopment.

Change in Strut Configuration

Figure 1A:
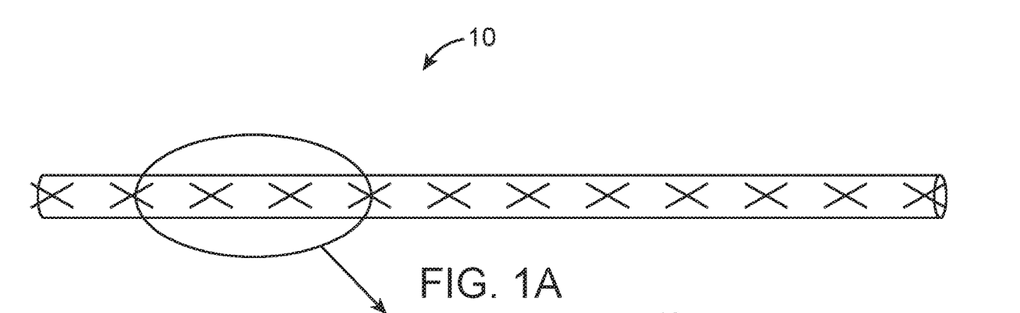
FIGS. 1A and 1B are perspective and detailed schematic views of an embolectomy device according to one embodiment in a radially compressed delivery configuration.
Figure 1B:
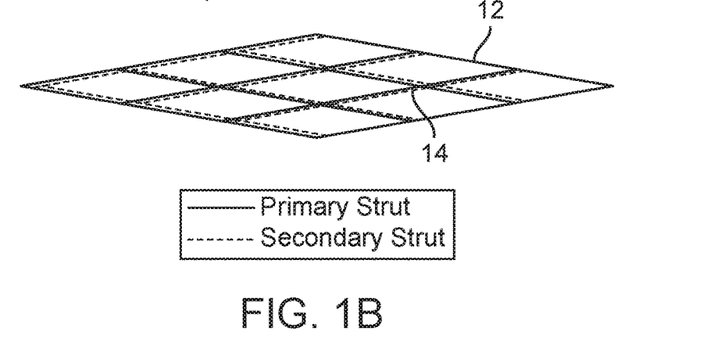

In the following embodiments, embolectomy device pore size is reduced after radial expansion of the embolectomy device by secondary struts 14 that move into the pores 16 from a position overlying respective primary struts 14, thereby partially bisecting the pore 16. FIGS. 1A to 3B show an embolectomy/clot-removing device 10 according to one embodiment of the disclosed inventions, wherein the device 10 is shown in various configurations during its deployment in a blood vessel. FIGS. 1A and 1B show the embolectomy device 10 in a radially compressed delivery configuration. Typically, embolectomy devices 10 are maintained in a radially compressed delivery configuration when constrained inside a tubular delivery catheter. As can be seen in inset FIG. 1B, when the embolectomy device 10 is in the delivery configuration, respective primary struts 12 of the device 10 are aligned and substantially overlap with respective secondary struts 14 of the device 10 to facilitate radial compression.

Figure 2A:
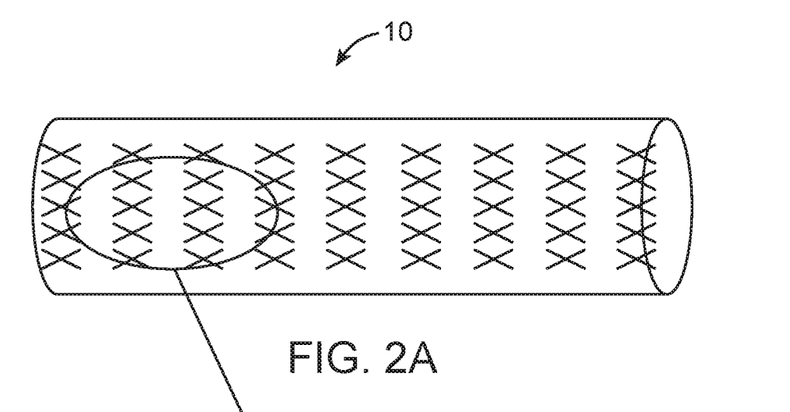
FIGS. 2A and 2B are perspective and detailed schematic views of the embolectomy device depicted in FIGS. 1A and 1B in a radially expanded configuration.
Figure 2B:
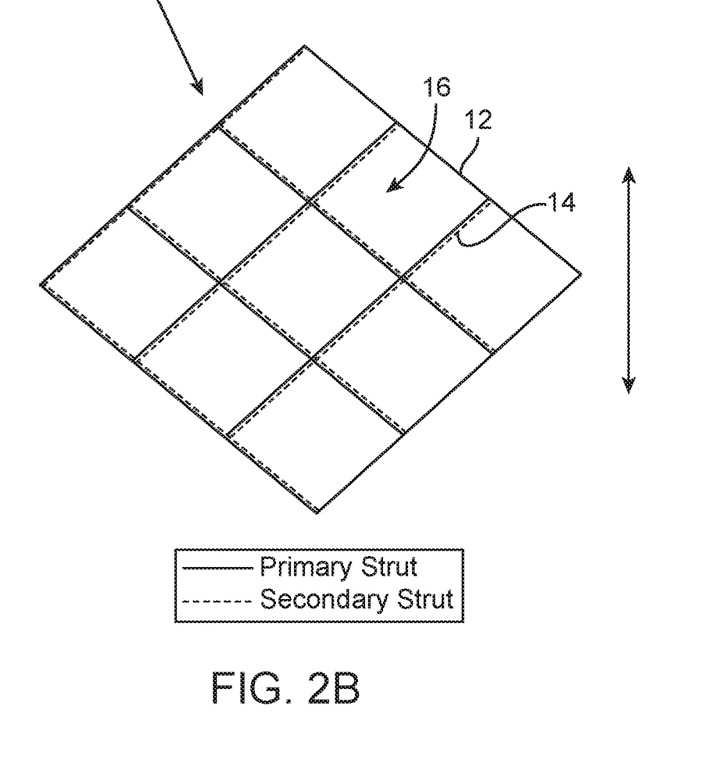

FIGS. 2A and 2B show the embolectomy device 10 after it has been released from the delivery catheter. Once it is no longer compressed and constrained in the delivery catheter, the embolectomy device 10 radially expands due to its elastic resilience, as shown in FIG. 2A. While undergoing the radial expansion, the embolectomy device 10 exerts a radially-outward directed force determined by the various components of the device, including respective the primary and secondary struts 12, 14. As seen in inset FIG. 2B, the primary and secondary struts 12, 14 remain aligned and substantially overlap each other after radial expansion. The overlapping primary and secondary struts 12, 14 together define a coarse mesh having relatively large windows or pores 16, such that obstructions, such as thrombi, in the blood vessel impart relatively low resistance to the radial expansion of the device 10.

Figure 3A:
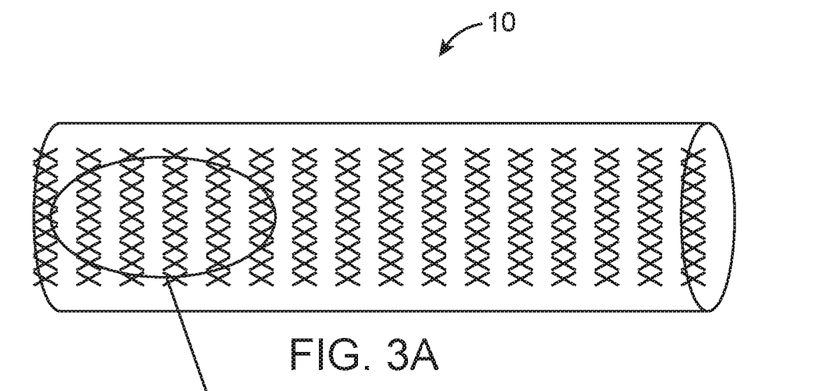
FIGS. 3A and 3B are perspective and detailed schematic views of the embolectomy device depicted in FIGS. 1A and 1B in a radially expanded and circumferentially expanded configuration.
Figure 3B:
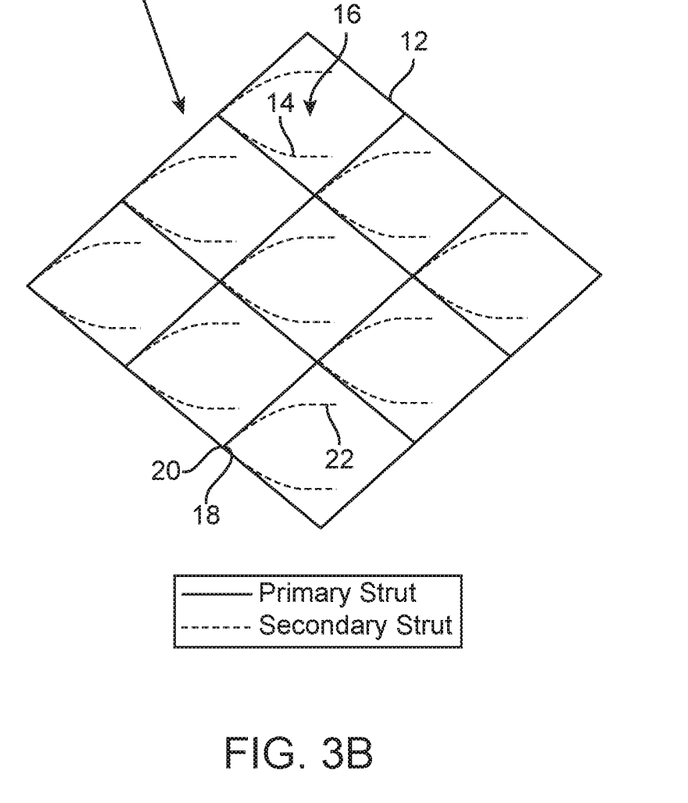

FIGS. 3A and 3B show the embolectomy device 10 after its initial deployment in the blood vessel, and full radial expansion has occurred. An actuator (i.e., trigger mechanism) is actuated, the secondary struts 14 of the embolectomy device 10 undergo a conformational change from the configuration depicted in FIG. 2A to the configuration depicted in FIG. 3A. During conformational change, the secondary struts 14 move into the pores 16, thereby partially bisecting the pore 16. The radius of the embolectomy device 10 does not vary significantly during the conformational change, but the mesh of the embolectomy device 10 becomes finer, and the windows become smaller. Inset FIG. 3B shows that, after the conformational change, the primary and secondary struts 12, 14 are no longer aligned. As shown in FIG. 3B, the secondary struts 14 include a fixed end 18 (permanently fixed to the primary struts 12 at a node 20) and a free end 22. After the conformational change, the free ends 22 of the secondary struts 14 extend into the pores 16, effectively creating a fine mesh with smaller pores 16. Smaller pores 16, in turn, results in increased resistance to passage of obstructions, such as thrombi, radially through the embolectomy device 10. Further, portions of obstructions can become trapped in the pores 16 as the pores 16 transition from being relatively larger in size to relatively to smaller in size, as the embolectomy device undergoes the conformational change.

The actuating or trigger mechanism for the conformational change of the secondary struts 14 can be a mechanical latch that restrains the secondary struts 14 in alignment with the primary struts 12 through interference with the secondary struts 14, which are biased to expand circumferentially. By way of example, the trigger mechanism can be automatically actuated by radial expansion of the embolectomy device 10, which would pivot the mechanical latch away from the free end 22 of the secondary strut 14. Configuring the trigger mechanism such that radial expansion actuates the conformational change avoids premature movement of the secondary struts 14 before radial expansion of the device 10 is at least well underway if not completed. Alternatively, the mechanical latch can be manually actuated to release the free ends 22 of the secondary struts 14 from outside of the patient.

In a related embodiment, the secondary struts 14 of the embolectomy device 10 form one way "flaps" that allow the obstruction or portions thereof to move into the embolectomy device 10 through the pores 16 defined by the primary struts 12. In this manner, once the obstruction or portions thereof have moved into the embolectomy device 10, the flaps (formed by the secondary struts 14) close around or into the obstruction to thereby capture or otherwise snare the obstruction and impede movement thereof out of the embolectomy device 10.

In another embodiment, the trigger mechanism for the conformational change is differential strut design. For instance, the primary and secondary struts 12, 14 may vary in circumferential or radial thickness, with the primary struts 12 being thicker. Alternatively, the primary and secondary struts 12, 14 may taper in the circumferential or radial directions and vary in the degree and/or rate of tapering, with the secondary struts 14 tapering more and/or more quickly. These examples of differential strut design will result in primary struts 12 recovering more quickly from elastic deformation than secondary struts 14.

In still another embodiment, the trigger mechanism takes advantage of different materials used for the primary and secondary struts 12, 14. For instance, the primary struts 12 may be made of material that is elastically deformed into the radially compressed delivery configuration (see FIG. 1A) and therefore biased to radially expand the embolectomy device 10 (see FIG. 2A). The secondary struts 14, on the other hand, can be made of a shape memory material, such that the low temperature shape of the secondary struts 14 is aligned with the primary struts 12 and the high temperature shape of the secondary struts 14 includes free ends 22 that extend into the pores 16 defined by the primary struts 12. The shape memory material from which the secondary struts 14 are formed is selected such that its transition temperature is near normal body temperature (37° C.). Accordingly, the shape memory secondary struts 14 begin their heat mediated conformational change after the embolectomy device 10 is delivered from the catheter into the vessel and the embolectomy device 10 is heated to body temperature by the blood therein. The delay (heating time) in the temperature induced transition to the austenite phase after delivery avoids accidental movement of the secondary struts 14 before radial expansion is at least well underway or completed.

Alternatively, the primary struts 12 can also be made of a shape memory material, but have a lower transition temperature than the material from which the secondary struts 14 are formed. Accordingly, as the embolectomy device 10 is heated by the blood, the austenitic transition of the primary struts 12 results in radial expansion before the austenitic transition of the secondary struts 14 results in movement of the secondary struts 14 into the pores 16.

In yet another embodiment, the trigger mechanism includes an adhesive which temporarily and reversibly fixes the free end of the secondary strut 14 to the primary strut 12, thereby holding the primary and secondary struts 12, 14 in alignment during delivery and radial expansion. In these embodiments, the secondary struts 14 are elastically deformed in alignment with the primary struts 12 such that their free ends 22 are biased to move into the pores 16 defined by the primary struts 12. After the embolectomy device 10 is delivered from the catheter into the vessel, the blood therein begins to dissolve the adhesive. When the adhesive is sufficiently dissolved, the bias of the elastically deformed secondary struts 14 overcomes the strength of the adhesive and the secondary struts 14 return to their relaxed positions with their free ends in the pores 16. The delay in the dissolving the adhesive after delivery avoids accidental movement of the secondary struts 14 into the pores 16 before radial expansion is at least well underway or completed.

In still another embodiment, the trigger mechanism takes advantage of materials used for secondary struts 14 that have a piezoelectric effect. The primary and secondary struts 12, 14 are aligned when the embolectomy device 10 is delivered from the catheter into the vessel. After the embolectomy device 10 is delivered and radially expanded by the bias of the primary struts 12, a current is applied to the embolectomy device 10 (through the delivery wire). The current generates an electric field, which triggers the free ends 22 of the secondary struts 14 to move into the pores 16 defined by the primary struts 12.

In another related embodiment, the current applied to the embolectomy device 10 after delivery heats (through resistive heating) the secondary struts 14, which are formed from a shape memory material. Heating the shape memory secondary struts 14 causes the secondary struts 14 to transition to their austenite phase and move their free ends 22 into the pores 16 defined by the primary struts 12. With this current mediated trigger mechanism, the user can wait until radial expansion is complete before applying the current to trigger movement of the secondary struts 14.

Change in Struts Dimension

In the following embodiments, embolectomy device pore size is reduced after radial expansion of the embolectomy device by increasing effective strut size. In one embodiment, current is applied to the embolectomy device 10 after delivery, which attracts ions that react with the metallic material from which the primary struts 12 are made to thicken the primary struts 12. In these embodiments, there are no secondary struts 14. Instead, the increase in thickness of the primary struts 12 decreases the size of the pores 16 defined thereby. With this current mediated trigger mechanism, the user can wait until radial expansion is complete before applying the current to trigger the increase in strut size and concomitant reduction in pore size.

In another embodiment, the primary struts 12 are coated with a localized coagulant, which thickens the primary struts 12 in blood due to coagulation. In this embodiment, there are no secondary struts 14. Instead, the increase in thickness of the primary struts 12 decreases the size of the pores 16 defined thereby. The delay in clot formation after delivery avoids accidental increases in strut size before radial expansion is at least well underway or completed. Coagulation may also adhere the obstruction (e.g., a thromboembolus) to the primary struts 12, thereby facilitating removal thereof by withdrawing the embolectomy device 10.

Relative Strut Movement

Figure 4A:
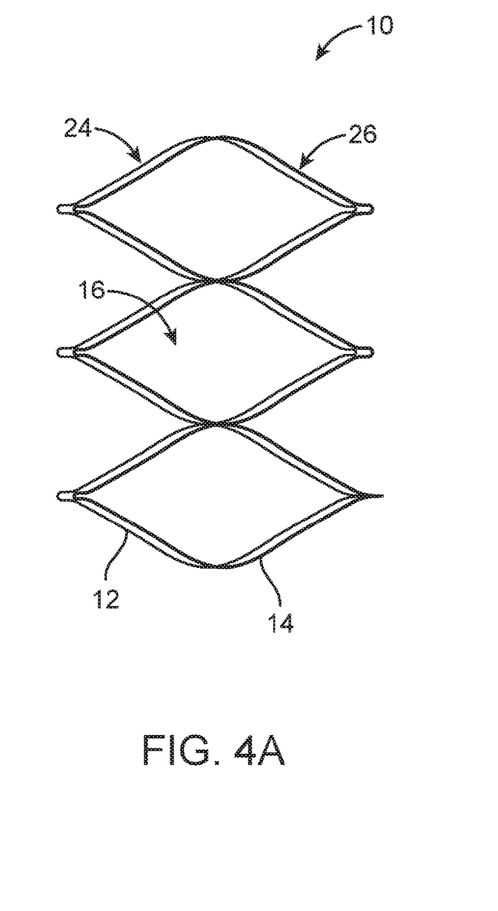
FIGS. 4A and 4B are detailed schematic views of a portion of an embolectomy device according to another embodiment in a radially expanded large pore configuration (FIG. 4A) and a radially expanded small pore configuration (FIG. 4B).

In the following embodiments, embolectomy device pore size is reduced after radial expansion of the embolectomy device by relative strut movement to define smaller pores 16. In one embodiment shown in FIGS. 4A to 6, the embolectomy device 10 includes concentric outer and inner tubular bodies 24, 26 made from primary and secondary struts 12, 14, respectively. The primary and secondary struts 12, 14 of the outer and inner tubular bodies 24, 26 define similar pores 16a and 16b. FIG. 4A depicts the embolectomy device 10 in its radially expanded configuration, which is achieved after the embolectomy device 10 is released from a delivery catheter at a target site. While FIG. 4A depicts the outer and inner tubular bodies 24, 26 as slightly offset from each other (to show two distinct tubular bodies 24, 26), in a preferred embodiment, the outer and inner tubular bodies 24, 26 are aligned such that they present a minimal radial profile. Alignment of the outer and inner tubular bodies 24, 26 and their respective primary and secondary struts 12, 14 results in a coarse mesh with larger pores 16. Larger pores 16, in turn, results in less resistance from obstructions, such as thrombi, during radial expansion.

Figure 4B:
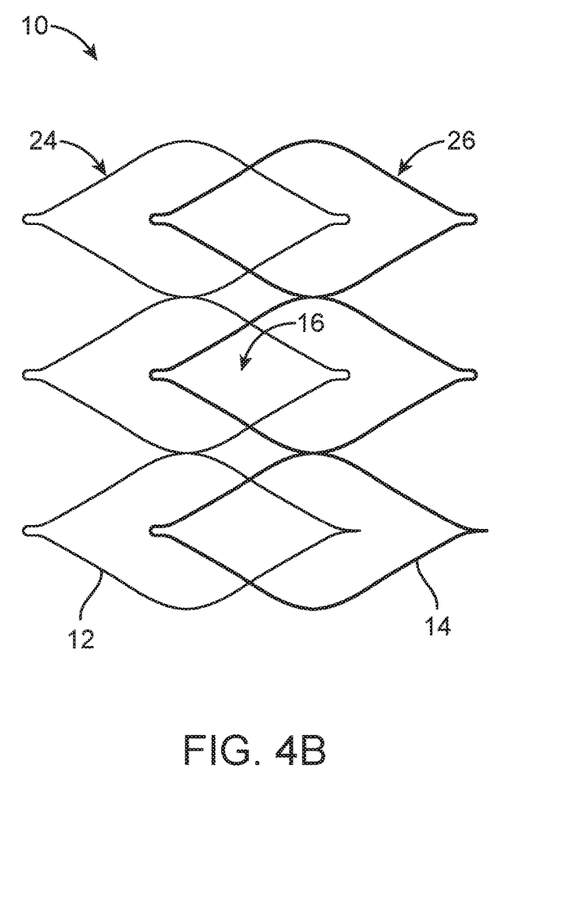

FIG. 4B depicts the embolectomy device 10 after it has been triggered to form smaller pores 16. The embolectomy device 10 is triggered to form smaller pores 16 by axially translating the inner tubular member 26 relative to the outer tubular member 24. While FIGS. 4A and 4B (and FIG. 6) depict only a series of three "cells" of each of the outer and inner tubular members 24, 26 (respectively defined by the primary and secondary struts 12, 14), the outer and inner tubular members 24, 26 each comprise other "cells" both in the axial and circumferential directions.

Figure 5A:
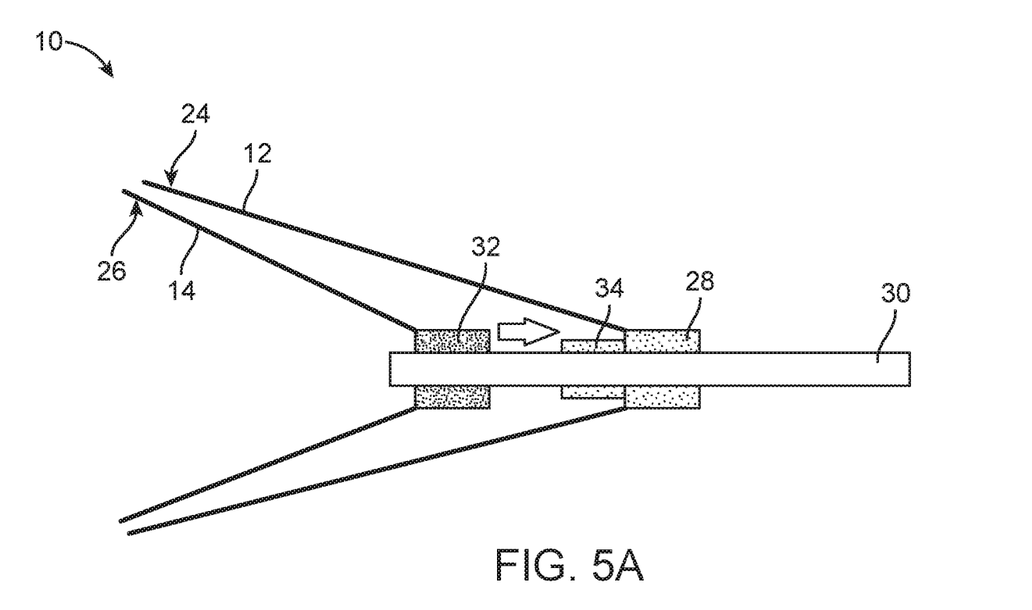
FIGS. 5A and 5B are detailed schematic views of another portion of the embolectomy device depicted in FIGS. 4A and 4B in a radially expanded large pore configuration (FIG. 5A) and a radially expanded small pore configuration (FIG. 5B).
Figure 5B:
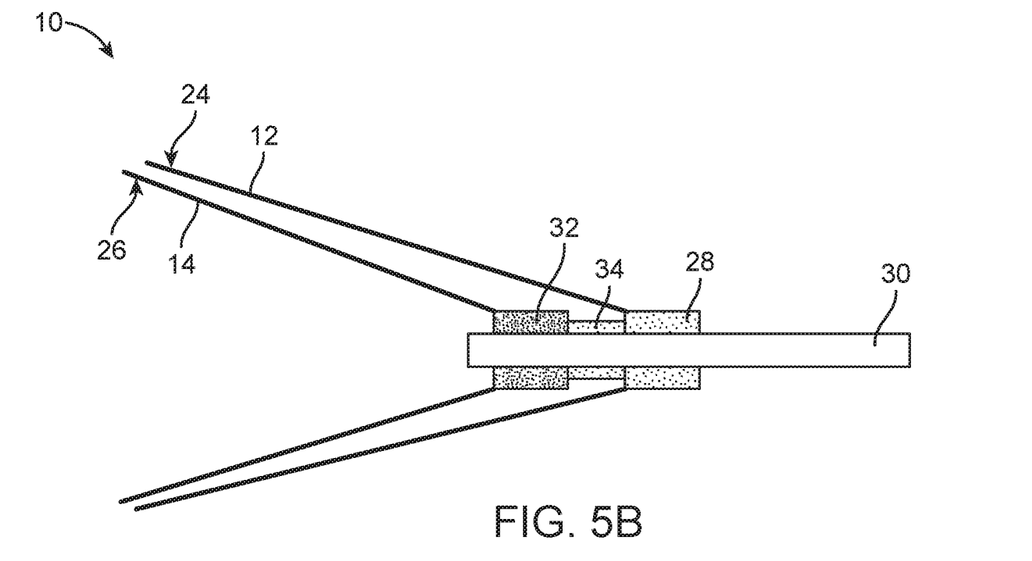

As shown in FIGS. 5A and 5B, the trigger mechanism includes an outer tubular member hub 28 permanently fixed to the outer tubular member 24 and temporarily and reversibly fixed to a delivery member 30. The outer tubular member hub 28 can be temporarily and reversibly fixed to the delivery member 30 by a connection that is removable by electrolysis or a solvent (e.g., blood), as shown in FIG. 5A. When the connection between the outer tubular member hub 28 and the delivery member 30 is removed, the outer tubular member hub 28 is slidably coupled to the delivery member 30 such that the outer tubular member hub 28 can slide along the delivery member 30, as shown in FIG. 5B. The trigger mechanism also includes an inner tubular member hub 32 permanently fixed to both the inner tubular member 26 and the delivery member 30. Further, the trigger mechanism includes a stopper 34 disposed on the delivery member 30 between the outer and inner tubular member hubs 28, 32. The stopper 34 may optionally be made of a deformable material and is configured to stop the relative movement of the outer and inner tubular member hubs 28, 32 toward each other (i.e., such that the stopper 34 acts as a spacer).

Figure 6:
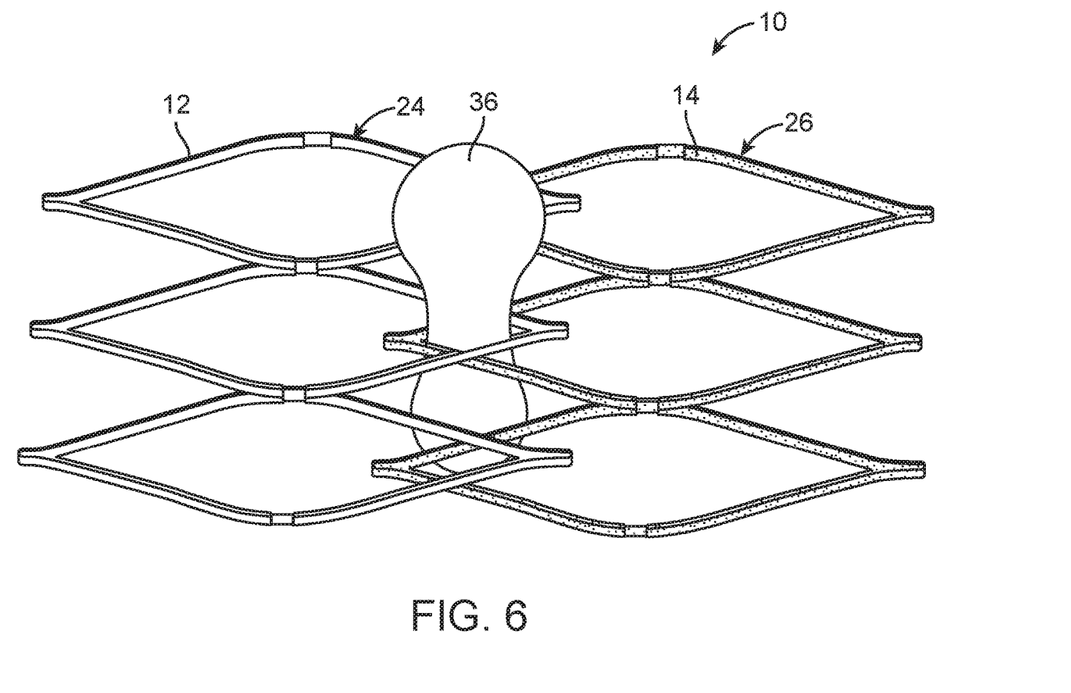
FIG. 6 is a detailed schematic view of another portion of the embolectomy device depicted in FIGS. 4A and 4B in a radially expanded small pore configuration with an ensnared vascular obstruction.

As shown in FIG. 6, when the embolectomy device 10 is radially expanded to contact a surface of a vascular obstruction 36 (e.g., a thromboembolus), a portion of the vascular obstruction 36 can protrude through a pore. When the embolectomy device 10 is triggered with a portion of the vascular obstruction 36 protruding through a pore 16, reducing the size of the pore 16 can trap the portion of the vascular obstruction 36 in the pore 16, thereby snaring the vascular obstruction 36 and fixing it to the embolectomy device 10. The user can wait until radial expansion is complete before triggering the embolectomy device 10 to form smaller pores 16 by axially translating the inner tubular member 26 relative to the outer tubular member 24.

In another embodiment, primary struts 12 are woven or braided together to form an embolectomy device 10 with floating points where primary struts 12 cross or overlap. Such a braided embolectomy device 10 can be formed by two counter-rotating wires roughly defining two helices. The braid can be configured such that the embolectomy device 10 has relatively large pores 16, even in its radially compressed delivery configuration. After radial expansion, the embolectomy device 10 can be axially compressed by pulling its distal and proximal ends toward each other. This can be accomplished by manipulating elongate members extending from respective distal and proximal ends. Axially compressing a braided embolectomy device 10 with floating primary struts 12 will result in relative movement of struts 12, thereby reducing pore 16 size.

Method of Manufacturing

A method of manufacturing embolectomy devices 10 such as those described above is to cut the embolectomy device 10 from one or more thin-walled tubular member, then to fix the other portions of the embolectomy device 10 (e.g., secondary struts 14 made from different materials, adhesives, and delivery members 30) thereto. An exemplary tubular member can be made from stainless steel. Cutting the tubular member removes unwanted portions of the tubular member to create openings to form the pattern of the embolectomy device 10.

The tubing from which the embolectomy device 10 is to be cut may be made of a suitable biocompatible material, such as stainless steel, nitinol, or other metals and polymers. Embolectomy devices 10 having complex shapes are cut from tubes that having outer diameters that are approximately the same as the outer diameters as the vessels into which they are to be implanted. A typical embolectomy device 10 has an outer diameter of about 0.5 mm (up to about 5 mm) in the unexpanded condition, and can be expanded to an outer diameter of about 2.5 mm or more. Accordingly, the tubing from which the embolectomy device 10 is made must have an outer diameter of about 1.5 mm (up to about 5 mm; the same as the unexpanded embolectomy device 10). A typical embolectomy device 10 wall thickness (and tubing wall thickness) is about 0.075 mm. Alternatively, the embolectomy device 10 can be braided or woven from elongate members.

Embolectomy Methods

A method 100 for removing a vascular obstruction 36 (e.g., a thromboembolus) using the various embolectomy devices 10 described above is depicted in FIG. 7. The target site in the method may be a neurovascular site, which is accessible only via a tortuous vascular path. Tortuous vascular paths contain a plurality of bends or turns which may be greater than 90° turns, and involve vessels which are less than about 8 mm, and as small as 2 mm to 3 mm, in diameter.

Figure 7:
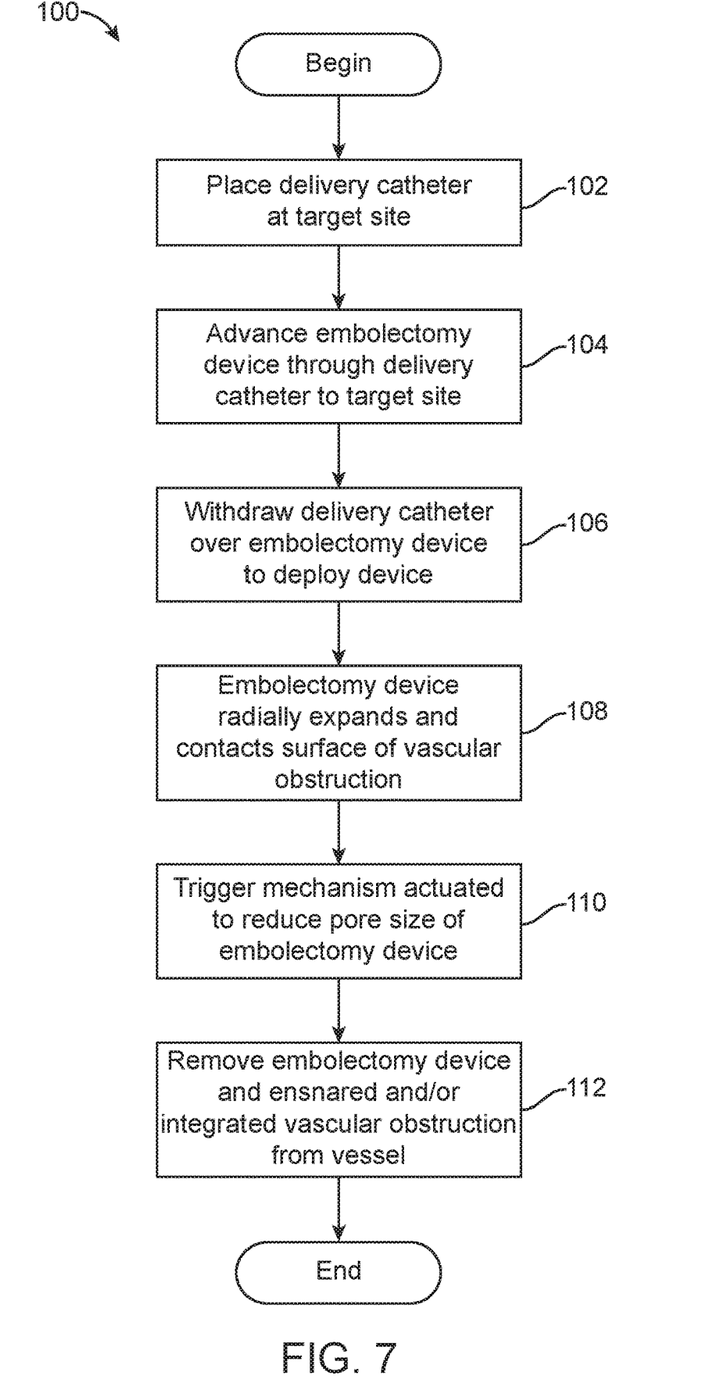
FIGS. 7 and 8 are flow charts showing methods of removing a vascular obstruction from a vessel according to two embodiments.

At step 102, a delivery catheter is placed at the target site according to known methods. Preferably, the delivery catheter is positioned at least partially across the vascular obstruction 36. A guidewire may be used to facilitate positioning of the delivery catheter. In a typical procedure for placing a delivery catheter at a target site, the delivery catheter and guidewire will advance through the path of least resistance, which is typically between the outer surface of the vascular obstruction 36 and the inner surface of the vessel.

At step 104, the embolectomy device 10, in its radially compressed delivery configuration, is introduced into a proximal end of the delivery catheter and advanced to the distal end of the delivery catheter. In embodiments including a guidewire, the guidewire is typically removed from the delivery catheter before the embolectomy device 10 is advanced through the delivery catheter. Radiopaque markers can be disposed on the delivery catheter and the embolectomy device 10 to facilitate placement thereof adjacent the vascular obstruction 36. Contrast agents can also be introduced into the vessel near the target site to improve visualization.

At step 106, the delivery catheter is withdrawn proximally over the embolectomy device 10 (which is held stationary) to deploy the embolectomy device 10 from the delivery catheter. At step 108, the deployed embolectomy device 10 radially expands and contacts a surface of the vascular obstruction 36 as shown in FIG. 6.

As shown in FIG. 6, a portion of the vascular obstruction 36 may protrude into the radially expanded embolectomy device 10 through a pore 16 (in the pore's 16 larger configuration). Struts 12, 14 from other portions of the embolectomy device 10 may move into and integrate into the vascular obstruction 36 at step 108. In most procedures, both ensnarement (where portions of the vascular obstruction 36 protrude into the embolectomy device 10 through a pore 16) and integration (where portions of the embolectomy device 10 protrude into the vascular obstruction 36) occur. The proportion of ensnarement to integration depends on the physical properties of the vascular obstruction 36, the vessel and the embolectomy device.

At step 110, the trigger mechanism is actuated, reducing the size of the pores 16 of the embolectomy device 10. Actuation of the trigger mechanism varies depending on the trigger mechanism. Several of the above-described trigger mechanisms (automatic mechanical latch, flaps, differential strut design, shape memory struts, adhesives, coagulant coating) are actuated by passage of time after deployment of the embolectomy device 10 out of the delivery catheter and into the vessel, which contains body temperature blood. Other trigger mechanisms described above (piezoelectric struts, resistive heating, ion-mediated strut thickening) require application of a current (e.g., through the delivery member 30) to the embolectomy device 10 after delivery. Still other trigger mechanisms described above (manual mechanical latch and dual tubular member design) require movement of portions of the embolectomy device 10 after delivery. However accomplished, reducing the pore 16 size increases the interference between the vascular obstruction 36 and the embolectomy device 10, thereby further ensnaring or integrating the vascular obstruction 36.

At step 112, with the vascular obstruction 36 ensnared by and/or integrated into the embolectomy device 10, the embolectomy device 10 is withdrawn proximally from the vessel and the patient to remove the vascular obstruction 36 therefrom. The embolectomy device 10 can be withdrawn into the delivery catheter, or another catheter, to facilitate its removal from the patient. Aspiration is typically applied during removal of the vascular obstruction 36 to minimize embolism of fragments of the obstruction 36. As the embolectomy device 10 is withdrawn proximally, its primary and secondary struts 12, 14 are moved into further engagement with the vascular obstruction 36.

One advantage of removing a vascular obstruction 36 by ensnarement or integration with an embolectomy device 10 is that protrusions from the vascular obstruction 36 (e.g., into side vessels) may also be removed along with the main body of the vascular obstruction 36.

Figure 8:
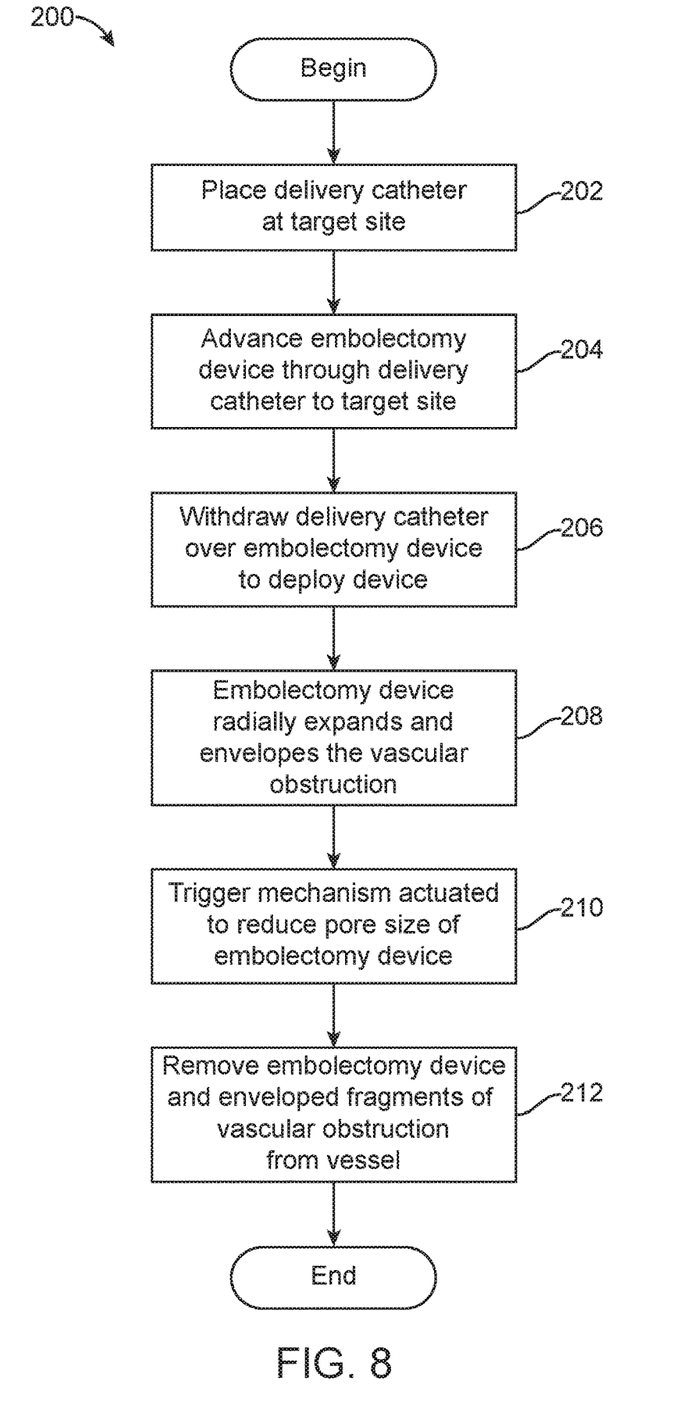

FIG. 8 depicts another method 200 for removing a vascular obstruction 36 (e.g., a thromboembolus) using the various embolectomy devices 10 described above. Steps 202, 204 and 206 of the method 200 are identical to corresponding steps 102, 104 and 106 of the method 100 depicted in FIG. 7 and described above.

At step 208, after the delivery catheter is withdrawn proximally over the embolectomy device 10 (which is held stationary) to deploy the embolectomy device 10 from the delivery catheter, the embolectomy device 10 radially expands. In step 208, the embolectomy device 10 radially expands to a diameter approximating the inner diameter of the vessel, substantially enveloping the vascular obstruction 36. The large pore 16 size and overlapping primary and secondary struts 12, 14 during step 208 facilitate passage of the vascular obstruction 36 into the embolectomy device 10 with minimal radially directed force. During passage of the vascular obstruction 36 through the large pores 16, the vascular obstruction 36 may be fragmented into large pieces. The embolectomy device 10 is selected so that its physical properties combine with the characteristics of the vascular obstruction 36 and the vessel (determined before the procedure) to maximize envelopment over integration during radial expansion.

At step 210, the trigger mechanism is actuated as described above with respect to step 110, reducing the size of the pores 16 of the embolectomy device 10. Reducing the size of the pores 16 generates a finer mesh that prevents most of the fragments of the vascular obstruction 36 from exiting the embolectomy device 10 during removal of the embolectomy device 10 and the vascular obstruction 36 from the vessel. To retain the fragments of the vascular obstruction 36 in the embolectomy device 10, the proximal and distal ends of the embolectomy device 10 can have smaller pores 16 than the middle of the embolectomy device 10, which is configured to envelop the vascular obstruction 36.

At step 212, the embolectomy device 10 and the fragments of the vascular obstruction 36 are withdrawn proximally from the vessel and the patient to remove the vascular obstruction 36 therefrom. The embolectomy device 10 can be withdrawn into the delivery catheter, or another catheter, to facilitate its removal from the patient. As the embolectomy device 10 is withdrawn proximally, it lengthens axially under the proximally directed force and its diameter is reduced as a result of the axial lengthening. Diameter reduction compacts the fragments of the vascular obstruction 36, further preventing their exit from the embolectomy device 10 and further facilitating their removal from the vessel.

The characteristics of the embolectomy devices 10 described above provide advantages over known devices. The larger pore 16 size during radial expansion allows snaring, integration and envelopment with a smaller radial force that an embolectomy device 10 that is radially expanded with smaller pores. The subsequent reduction of pore 16 size increases snaring and integration of the obstruction (blood clot or calcification), and also helps to prevent fragments from exiting in the case of clot envelopment. The disclosed embodiments of the embolectomy devices 10 also help to reduce rolling of the obstruction external to the embolectomy device 10. The envelopment method 200 minimizes movement of emboli to side branch vessels and distal of the original obstruction 36. The envelopment method also reduces (and potentially eliminates) the need for aspiration during removal of the vascular obstruction 36. The overlap of the primary and secondary struts 12, 14 during radial expansion reduces fragmentation and maceration of the vascular obstruction 36. The overlap of the primary and secondary struts 12, 14 during radial expansion also reduces the radial force necessary to envelop the vascular obstruction 36, thereby reducing vessel wall trauma. The secondary struts 14 and their free ends 22 also reduce radial force and vessel wall trauma.

While FIG. 8 depicts an embolectomy method 200 for removing a vascular obstruction 36 by enveloping the vascular obstruction 36, embolectomy methods may include both envelopment and ensnarement to varying degrees for removal of vascular obstructions.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense.

What is claimed is:

1. An embolectomy device for removing an obstruction from a vascular site, comprising:
    a first tubular body having a radially collapsed configuration and a radially expanded configuration, the first tubular body comprising a first plurality of interconnected struts that define a first plurality of openings when the first tubular body is in the radially expanded configuration;
    a second tubular body having a radially collapsed configuration and a radially expanded configuration, the second tubular body comprising a second plurality of interconnected struts that define a second plurality of openings when the second tubular body is in the radially expanded configuration, wherein the first and second tubular bodies are coaxially disposed; and
    an elongate actuator having a distal portion attached to a proximal hub of the first tubular body, wherein the elongate actuator passes through a hub of the second tubular body proximal to the proximal hub of the first tubular body, so that proximal movement of the elongate actuator moves the first tubular body proximal relative to the second tubular body, the embolectomy device having
    a delivery configuration in which the first and second tubular bodies are in their respective radially collapsed configurations,
    a deployed configuration in which the first and second tubular bodies are in their respective radially expanded configurations with the first plurality of struts and openings substantially aligned with the second plurality of struts and openings, and
    an actuated configuration in which the first and second tubular bodies have been moved axially relative to one another by the elongate actuator so that the first plurality of struts and openings are off-set with the respective second plurality of struts and openings,
    such that, when the embolectomy device is delivered to a targeted vascular site proximate an obstruction, moved or allowed to move from the delivery configuration to the deployed configuration with the respective first and second tubular bodies expanding radially into or through the vascular obstruction, and thereafter moved from the deployed configuration to the actuated configuration, portions of the vascular obstruction become ensnared and/or encapsulated between or within the respective first and second pluralities of struts.

2. The embolectomy device of claim 1, further comprising a stop member positioned on the elongate actuator between the proximal hub of the first tubular body and the hub of the second tubular body.

3. A method of removing a vascular obstruction, comprising:
    introducing the embolectomy system of claim 1 into a blood vessel proximate the obstruction to be removed;
    allowing the embolectomy system to self-transition from the delivery configuration to a deployed configuration in which the first and second tubular bodies are in their respective radially expanded configurations with the first plurality of struts and openings substantially aligned with the second plurality of struts and openings; and
    translating the elongate actuator axially so as to axially translate the first tubular body axially relative to the second tubular body to place the embolectomy system in an actuated configuration in which the first plurality of struts and openings are off-set with the respective second plurality of struts and openings,
    wherein when the embolectomy system is moved from the deployed configuration to the actuated configuration, portions of the vascular obstruction become ensnared and/or encapsulated between or within the respective first and second pluralities of struts.

* * * * *